US005474900A

United States Patent [19]
Ishikawa et al.

[11] Patent Number: 5,474,900
[45] Date of Patent: Dec. 12, 1995

[54] **PROCESS FOR PREPARING PURIFIED SYPHILIS ANTIGEN FROM *TREPONEMA PALLJDUM***

[75] Inventors: Fumio Ishikawa, Takatsuki; Kouhei Nagahara, Kamaishi; Mie Matsumoto, Moriyama, all of Japan

[73] Assignee: Sekisui Chemical Co., Ltd., Osaka, Japan

[21] Appl. No.: 271,776

[22] Filed: Jul. 7, 1994

Related U.S. Application Data

[63] Continuation of Ser. No. 985,346, Nov. 30, 1992, abandoned, which is a continuation of Ser. No. 704,526, May 24, 1991, abandoned, which is a continuation-in-part of Ser. No. 669,479, Mar. 14, 1991, abandoned.

[30] Foreign Application Priority Data

Mar. 16, 1990 [JP] Japan .................................... 2-67986

[51] Int. Cl.$^{6}$ .......................... C12P 21/00; G01N 33/531

[52] U.S. Cl. .............................................. 435/71.1; 45/7.1

[58] Field of Search .................................. 435/7.36, 71.1

[56] References Cited

U.S. PATENT DOCUMENTS

| | | | |
|---|---|---|---|
| 2,892,755 | 6/1959 | Portnoy | 435/7.36 X |
| 3,951,937 | 4/1976 | Unek et al. | 530/380 |
| 4,427,782 | 1/1984 | Caldwell et al. | 436/542 |
| 4,618,588 | 10/1986 | Sato et al. | 436/511 |
| 4,839,277 | 6/1989 | sugahara et al. | 435/5 |
| 4,849,358 | 7/1989 | Chazono et al. | 435/252 |
| 4,868,118 | 9/1989 | Norgard | 435/252.33 |
| 4,894,328 | 1/1990 | Alderete et al. | 435/7.36 |
| 4,973,551 | 11/1990 | Condra | 435/69.7 |
| 5,028,694 | 7/1991 | Mewman et al. | 530/350 |

FOREIGN PATENT DOCUMENTS

| | | |
|---|---|---|
| 0038150 | 10/1981 | European Pat. Off. . |
| 0079145 | 10/1982 | European Pat. Off. . |
| 0138167 | 4/1985 | Europe Pat. Off. . |
| 2233024 | 6/1974 | France . |
| 8703692 | 12/1986 | WIPO . |

OTHER PUBLICATIONS

Brooks (1981) "Hydroxylapatite, Fast Flow and High Resolution", Behring Diagnostics, San Diego.

Genitourin Med. vol. 62, 1986, (London) pp. 367–372, Van Eijk et al. "Enzyme Linked Immunosorbent Assays with Treponema Pallidum or Axial Filament of T Phagednis . . . ".

*Primary Examiner*—Marian C. Knode
*Assistant Examiner*—Jon P. Weber
*Attorney, Agent, or Firm*—Merchant, Gould, Smith, Edell, Welter & Schmidt

[57] ABSTRACT

A process for preparing a purified syphilis antigen from *Treponema pallidum* is presented. The process comprises the steps of obtaining an extract from *Treponema pallidum*, adsorbing the extract onto hydroxyapatite gel and eluting the antigen in the presence of a surfactant. The preferred surfactant is octylglucopyranoside, A diagnostic agent is prepared which comprises the purified syphilis antigen adsorbed on an inert carrier, which carrier at least partially a hydrophobic carrier to which the antigen is adsorbed.

6 Claims, No Drawings

PROCESS FOR PREPARING PURIFIED SYPHILIS ANTIGEN FROM *TREPONEMA PALLIDUM*

This application is a continuation of U.S. application Ser. No. 07/985,346 filed Nov. 30, 1992, now abandoned, is a continuation of U.S. application Ser. No. 07/704,526 filed May 24, 1991, now abandoned, which is a continuation-in-part of Ser. No. 07/669,479 filed Mar. 14, 1991, abandoned.

BACKGROUND OF THE INVENTION

1. Field of the Invention

The present invention relates to a process for preparing an antigen of Treponema (*Treponema pallidum*, hereinafter sometimes abbreviated to TP) which is used as a reagent for diagnosing syphilis. More particularly, the present invention relates to a method for preparing an antigen which enables to prepare a diagnostic agent for syphilis, exhibiting high specificity and being able to detect primary syphilis. Further, this invention relates to a diagnostic reagent for syphilis and a method for preparing the same.

2. Prior Arts

Diagnostic methods have been performed which utilize the antigen-antibody reaction of TP antigens and anti-treponemal antibodies (hereinafter abbreviated to TP antibody) in sera from syphilitic patients. Among such methods, TPHA (*Treponema pallidum* hemaggultination assay test) has been widely used in recent years because of the advantages in its sensitivity, specificity and convenience in operation. Therefore, the TPHA has been a typical diagnostic method for syphilis.

The antigen solution originated from TP and used in the above-mentioned method is prepared as follows: First, TP is inoculated and cultivated in rabbit testes. The treponemes are extracted and suspended in a suitable buffer and then disrupted by homogenizer, sonicator and so forth. Thus disrupted treponemes with or without solubilization was used as the antigen solution for sensitization.

However, the prior art has the following drawbacks. Specifically, primary syphilis can not sufficiently be detected by the diagnostic agent for syphilis made from the conventional TP antigen solution. In other words, the conventional TPHA test or the like does not show a positive result in most cases until 2 to 3 months after syphilitic infection. Accordingly, there is a great problem that, in order to accomplish reliable diagnosis for primary syphilis, a diagnostic reagent using a lipoidal antigen (cardiolipin) should be used together with the TPHA method. Although the reagent using lipoidal antigens is sensitive to primary syphilis, nonspecific reactions are often observed.

In a syphilitic antibody detection test such as TPHA, sensitivity of reagent to a primary antibody (Ig-M) is lower than an advanced antibody. This was caused by impurities in the antigen solution used for the reagent. Namely, in the conventional TPHA, the TP antigen solution used for sensitization of animal erythrocytes inevitably includes impurities due to the preparation method. 90% or more of impurities are proteins originated from rabbit testes in which TP is cultivated, or from TP components having no antigenicity. Consequently, a significant quantity of impurities is incorporated in the TP antigen solution, so that the primary antibody (Ig-M) cannot be detected.

The antigen solution used for the conventional TPHA inevitably includes components originated from rabbit tissue due to its preparation method, which cause nonspecific reaction. Therefore, in order to reduce the nonspecific reaction, some components originated from rabbit tissue were added to the buffer of TPHA for absorbing heterophil antibodies in serum to be tested.

In order to solve the above-mentioned problems, Japanese Unexamined Patent Application No. SHO 58(1983)-71457 discloses a technique using an antigen fraction which is obtained by removing fractions having specific gravity of 1.01 or less from the extracted treponemal suspension.

However, a significant quantity of impurities is still mixed in the antigen fraction, because the fractionation method by the difference of specific gravity does not provide a strict separation of the antigen fraction from rabbit tissue. The aforesaid Japanese Application states that the above method is applicable even after the disruption of treponemes. However, sodium diatrizoate or the like used for density gradient reagents is inevitably incorporated in the antigen solution in this method, and hence, a process for removing the density gradient reagents should be required. Accordingly, this method would not be applied after the disruption of treponemes.

An immunological diagnostic reagent is generally prepared by immobilizing an antigen or antibody on a hydrophobic carrier (e.g., plastic particles such as latex particles, cellulose powder, polystyrene, polypropylene or nylon particles; membrane of nitro-cellulose or nylon; erythrocytes treated with tannic acid; or agarose gel). Known immobilization methods include a method by physical adsorption wherein an antigen or antibody is in contact with a hydrophobic carrier in an aqueous medium and a method wherein an antigen or antibody is covalently bonded to a carrier having an amino group or a carboxylic group on its surface. The former method utilizing physical adsorption is widely used in view of manufacturing efficiency, convenience and being easy to reproduce the product of the same quality.

In the case of immobilizing an antigen or antibody by physical adsorption, an approximately neutral buffer comprising a salt and a buffering agent is usually used as the aqueous medium. A surfactant is not employed as the aqueous medium, since the surfactant is considered to interfere with the immobilization of antigen or antibody on carrier. Specifically, the surfactant is considered to decrease the hydrophobic interaction in immobilization by physical adsorption.

The surfactant is also considered to interfere with the immobilization of TP antigens on carriers. In other words, the efficiency of immobilization is substantially decreased in the presence of the surfactant, with the result that it is difficult to prepare an excellent diagnostic reagent.

SUMMARY OF THE INVENTION

The present invention is accomplished to solve the problem of impurities in the antigen immobilized on the carrier in the method for preparing the antigen originated from *T. pallidum*. A main object of the present invention is to provide a process for preparing a treponemal antigen used for a diagnostic agent of syphilis which can detect a primary syphilis as well as an advanced syphilis and does not exhibit a nonspecific reaction.

Thus, the present invention provides a process for preparing a treponemal antigen which comprises adsorbing an extract originated from *T. pallidum* on a hydroxyapatite gel, followed by elution, while an aqueous medium is used.

Further, the present invention provides a diagnostic agent employing a treponemal antigen, preferably the above-mentioned one and a method for preparing the same.

The diagnostic agent of syphilis in the present invention comprises a treponemal antigen and a carrier. Preferably, the agent is prepared by treating a carrier with a treponemal antigen in an aqueous medium having a pH from about 4.5 to about 7.7 and containing a surfactant in an amount of from about 0.01 wt. % to about 2.5 wt. % and removing the remaining surfactant if any.

PREFERRED EMBODIMENT OF THE PRESENT INVENTION

The extract originated from *T. pallidum* can be prepared in accordance with the present invention as follows.

(1) Selection, cultivation and collection of *T. pallidum*

Suitable seed strain of *T. pallidum* is, for example, WHO's pathogenic standard Nichols strain or *T. pallidum* strain used for diagnosing syphilis in various tests. The WHO's pathogenic standard Nichols strain is easily available from, for example, CDC (Center for Disease Control, Public Health Service, U.S. Department of Health, Education and Welfare, Atlanta Ga.). The cultivation, collection and treatment methods can optionally be selected among any known methods.

(2) Disruption and solubilization of TP

Subsequently, the collected treponemes are suspended in a buffer solution. After cooling and disruption, the resultant is solubilized to obtain the extract originated from TP. The method for disruption or solubilization is optionally selected among any known methods. The disruption can be conducted by a homogenizer, ultrasonication or freeze-thawing method. The solubilization can be performed with a surfactant for solubilization of slightly soluble protein, chaotropic ion (e.g., $SCN^-$, $Cl^-$ or $I^-$), urea or an alkaline treatment, an enzymatic treatment, an autolysis method or the like. Particularly, the solubilization method is more suitable which employs a now ionic strength buffer containing a non-ionic or amphoteric surfactant.

Besides, the present method is applicable to an extract containing TP antigen which is obtained from *Escherichia coli* or the like in accordance with a recombinant DNA method, as far as said antigen has the physicochemical characteristics existing within the range of those of the antigen of the present invention.

(3) Pretreatment

It is preferable that any pretreatment is carried out for removing impurities beforehand as much as possible from the extract originated from TP in order to effectively perform the present invention. of course, the present invention can be carried out without the pretreatment.

Examples of the pretreatment are as follows:

(a) The fractions other than the antigen fraction are removed beforehand by an ion-exchange chromatography (utilizing, for example, a cation exchanger).

(b) A partial purification is conducted with a sodium sulfate or polyethylene glycol fractination.

The above pretreatment (a) is more desirable since it is easier to perform compared with (b).

A preferable embodiment will be explained hereinbelow for performing the method for preparing the treponemal antigen according to the present invention. It is to be noted that the present invention should not be limited to the embodiment described below.

(1) Hydroxyapatite gel

The hydroxyapatite used in the present invention can be represented by the chemical formula of $[Ca_5(PO_4)_3(OH)]_2$.

Usable gels are those on market, for example, Bio-Gel® HTP (Bio-Rad Laboratories) or HCA-200 L (Mitsui Toatsu Chemicals, Inc.). There is no limitation in the shape and the particle size of the gel. Generally, gels for column chromatography can be used. Preferably, the specific surface area of the gel is about 1 to 100 $m^2/g$ and the particle size thereof is about 1 to 100 μm.

(2) Kind of the aqueous medium

Any buffer used for general biochemical experiment such as phosphate buffer, Tris buffer, glycine buffer or the like can be used as the aqueous medium in the present invention. Phosphate buffer is preferable.

(3) pH of the aqueous medium (a) Adsorption of the antigen

The pH of the aqueous medium is preferably within the range from about 5.0 to 8.0, more preferably within the range from about 5.5 to 7.0. When the pH is less than 5.0, antigenicity is likely to be lost, thereby decreasing recovery of the TP antigen. On the other hand, the aqueous medium having pH 8.0 or more causes the reduction in the adsorption efficiency of the antigen to the hydroxyapatite gel, thereby decreasing recovery of the TP antigen.

(b) Elution of the antigen

The pH is preferably within the range from about 5.0 to 11.0, preferably about 5.5 to 10.0 for eluting the antigen. When the buffer has pH 8.0 or more, its ionic strength is preferably to be in a low ionic strength such as 10 to 60 mM to reduce the affinity of antigen for the column. When the pH is less than 5.0, antigenicity is likely to be lost, thus undesirable. On the other hand, an aqueous medium having a pH more than 11.0 tends to elute the impurities together with the antigen, thus undesirable.

(4) Ionic strength of the aqueous medium (a) Adsorption of the antigen

An aqueous medium having an ionic strength of preferably about 2 to 30 mM, more preferably about 10 to 20 mM is used to adsorb the extract originated from TP on the hydroxyapatite gel.

When the ionic strength is less than 2 mM, it is not practical because impurities tend to be adsorbed on the hydroxyapatite gel and the capacity of the buffer used is reduced. On the other hand, when the ionic strength is more than 30 mM, it causes less adsorption of the antigen on the hydroxyapatite gel, thereby decreasing the recovery.

(b) Elution of the antigen

The ionic strength in the elution is preferably about 10 to about 360 mM, more preferably about 50 to about 120 mM. When the ionic strength is less than 10 mM, the antigen is hard to be eluted at an acidic pH. The impurities are also eluted with an ionic strength of more than 360 mM, thus undesirable. In case where the elution is conducted with an ionic strength below that in the adsorption, the elution is preferably carried out at a pH higher than that in the adsorption. On the other hand, the elution is preferably carried out with an ionic strength higher than that in the adsorption in case where the elution is conducted with a pH below that in the adsorption.

(5) Additive or the like to the aqueous medium

Any materials to which the hydroxyapatite gel is resistant such as the surfactant, chaotropic ions or urea which can be used for solubilization of treponemal antigen can be used as the additive to the aqueous medium for the adsorption and elution. A buffer of low ionic strength which contains a non-ionic or amphoteric surfactant is preferably used for the method of the present invention in consideration of easiness of operation. Besides, the use of chelating agent such as EDTA is not recommended since it interferes with the adsorption of the antigen protein to the hydroxyapatite gel.

(6) Gradient elution

The elution can be carried out with stepwise or linear increase of the ionic strength or pH, although the increasing pattern is not particularly limited.

The stepwise increasing method would be industrially effective, because the antigen can be once eluted under a predetermined suitable condition. However, in such method, it is noted that the perfect separation of the antigen from impurities may not be attained in some cases. Accordingly, the linear gradient elution method which linearly increases the ionic strength and/or pH is preferable. By this method, the optimal fraction can be obtained by examining the elution profile on chromatogram, or dividing the fractions as detailedly as possible and measuring the antigen activity thereof.

By the present method, the substantially pure antigen can be obtained.

When the extract originated from treponemes is in contact with the hydroxyapatite gel in the buffer having a low ionic strength (salt concentration), the antigens are adsorbed on the gel. Then, the antigens are eluted from the gel at the ionic strength within the predetermined range, thereby obtaining the antigen of high-purity.

Explained next is the application of the antigen obtained by the present invention.

(1) Diagnostic agent and a method for preparing the same

The treponemal antigens of the present invention are immobilized on a carrier by any known method to make a reagent for diagnosing syphilis.

Any carrier used in this field can be used. Preferable carriers are inert carriers in which the surface is at least partially hydrophobic. Examples of the carriers are synthetic polymer particles having a particle size of about 0.05 to 50 μm prepared by performing polymerization or copolymerization with a monomer such as styrene, acrylic acid, methyl methacrylate, acrylonitrile or butadiene and particularly microparticles having an uniform particle size of 0.1 to 2 μm, i.e., latex particles called in the field of an immunological diagnostic reagent, prepared by emulsion-polymerizing the aforesaid polymer or its derivatives in an aqueous medium; synthetic polymer materials such as polystyrene, polyethylene, polypropylene, nylon or cellulose acetate and their molded product; membrane of nylon, nitrocellulose or the like; materials of living organism such as sheep or hen erythrocytes treated with tannic acid; and inorganic materials such as silica powder or glass particles, or the like. The latex particles and erythrocytes treated with tannic acid are more preferable.

"The surface is at least partially hydrophobic" means the property for immobilizing the antigen via any physical adsorption. The surface may entirely be hydrophobic. Some materials may be used by activating the surface thereof.

According to the present invention, it is found that the immobilization of the antigen on a carrier is conducted in contacting them in an aqueous medium containing about 0.01 to 2.5% by weight of a surfactant and having pH about 4.5 to 7.7, thereby providing a reagent with excellent sensitivity and improved specificity in which the antigens are much stably immobilized.

Besides, in case where the surfactant is used at a high concentration, it is preferable to remove the possibly remaining surfactant after the immobilization, in order to avoid the interference of the surfactant with the antigen-antibody reaction.

Usable surfactants for the above immobilization are those which can be used for extraction and stabilization of the surface antigen and membrane protein of TP, are capable of extracting and solubilizing the object constituents, have high specificity of extractability, and are stable at pH about 4.5 to 7.7 without separation. Preferable examples of the surfactants are non-ionic surfactants such as octylglucopyranoside (1-O-n-octyl-β-D-glucopyranoside), Triton X-100®, Tween 20®, Tween 80®, octylthioglucoside or the like or ampholytic surfactants such as CHAPS (3-[(3-Cholamidopropyl)dimethyl-ammonio]-1-propanesulfonate) or the like. Cationic surfactants such as dodecylamine or anionic surfactants such as sodium dodecyl sulfate can be used.

The effective concentration of the surfactant in the aqueous medium for immobilizing the TP antigen on the carrier is about 0.01 to 2.5 wt. %, preferably about 0.02 to 2.10 wt. %. If the concentration of the surfactant is higher, the TP antigen cannot be immobilized on the carrier. The activity of the TP antigen is likely to be lost with the surfactant of lower concentration.

Preferable examples of the aqueous media used for immobilizing the TP antigen on the carrier are buffers used for general biochemical experiments, e.g., phosphate buffer, Tris buffer or the like. The ionic strength is adjusted by the addition of salt to the aqueous medium. The effective pH is about 4.5 to 7.7, preferably about 4.9 to 7.1, more preferably about 5.4 to 6.5. If the pH is less than 5.0, antigenicity is likely to be lost, but the adsorption is performed instantaneously. Thus, the pH may be more than 4.5. The quantity of the TP antigen immobilized on the carrier becomes less with the aqueous medium of pH more than 7.7. In order to increase the storage stability of the obtained diagnostic reagent, a preservative can be added thereto if necessary.

Further, choline chloride, EDTA, saccharides (polysaccharide, dextran or the like), polyethylene glycol and the like can be added in order to improve the sensitivity in measurement.

Explained subsequently is a specific method for treating the carrier with the antigen solution.

First, the antigen solution for immobilization is prepared by any known method. For example, the treponemes are extracted from rabbit testicular materials containing treponemes. Then, the treponemes are washed, to which a surfactant is added. The resultant mixture is incubated to disrupt the treponemes and extract the TP antigen. The extract is centrifuged to collect the supernatant which is then diluted with a buffer containing a surfactant to obtain treponemal antigen solution. The obtained solution is adjusted to have a predetermined surfactant concentration and pH, thus making the sensitizing solution, i.e., the antigen solution for immobilization.

Subsequently, the sensitizing solution is in contact with the carrier described above in an aqueous medium containing about 0.01 to 2.5 wt. % of surfactant and having pH about 4.5 to 7.7. The resultant mixture was incubated for a predetermined period to immobilize the TP antigen on the carrier.

Other methods for immobilizing the TP antigen on the carrier include various ones, e.g., a method in which an antigen solution containing a suitable concentration of surfactant is added to a carrier suspension containing or not containing surfactant to adjust the concentration of surfactant and pH to a predetermined value, and then results in immobilization of the antigens, or a method in which a carrier is contacted with an antigen solution and then a diluent comprising a surfactant or buffer is added to adjust the concentration of surfactant and pH to a predetermined value thereby immobilizing the TP antigen.

After the immobilization, the carrier is separated from the aqueous medium and then washed with a buffer containing bovine serum albumin, saline solution or the like to remove the surfactant.

The antigen sensitizing solution described above is prepared from a so-called partially purified antigen fraction. An excellent diagnostic reagent can be obtained as mentioned below by using the treponemal antigen purified according to the present invention with the carrier of latex particles.

The surfactant used for immobilizing the antigen on the carrier in the present invention is considered to stabilize the antigens in the antigen solution and prevent unnecessary components in the material from being immobilized on the carrier. In general, the surfactant interferes with the immobilization of antigens on carriers. The antigens of the present invention are slightly soluble in water and hence low isoelectric points, whereby the solubility of the antigen is decreased by lowering pH so that the immobilization on carrier occurs even in the presence of the surfactant. As a result, the dignostic reagent of the present invention has an increased amount of the antigen carried on the carrier and more excellent sensitivity compared with that prepared by the conventional method. Further, amount of other components immobilized the carrier decreases, thereby improving specificity.

(2) Application of the diagnostic reagent

The disgnostic agent of the present invention is used for detecting anti-treponemal antibodies in the subject serum. The detection methods include radio-immunoassay (RIA), fluorescent immunoassay (FIA), enzyme immunoassay (EIA or ELISA), latex agglutination assay, TPHA method (*Treponema pallidum* hemaggultination assay test) or the like. The diagnostic reagent of the present invention can be formed to suit the above-mentioned detection methods.

The immunoassay utilizing the antigen-antibody reaction is preferably conducted in the presence of a water-soluble polymer and/or water-soluble copolymer containing at least one kind of glycoside derivatives represented by the following formula (I) as a monomer:

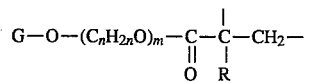

$$G-O-(C_nH_{2n}O)_m-\underset{\underset{R}{|}}{\overset{\overset{O}{\|}}{C}}-\overset{|}{C}-CH_2- \quad (I)$$

wherein G—O— represents a saccharic residue not having a protective group. R is a hydrogen atom, a methyl group or an ethyl group, m is an integer of 1 to 3 and n is an integer of 1 to 4.

The saccharic residue in the above glycoside derivative is a group in which a hydrogen atom is removed from a hydroxyl group bonded to the glycosidic carbon atom of the reduced end of a saccharide. Specifically, the saccharic residue means a residue of a monosaccharide comprising 1 to 3 sugar units or an oligosaccharide.

Examples of the monosaccharides are hexoses such as glucose, mannose, galactose, glucosamine, mannosamine or galactosamine, or pentoses such as arabinose, xylose or ribose.

Examples of the oligosaccharides are disaccharides such as maltose, lactose, trehalose, cellobiose, isomaltose, gentiobiose, melibiose, laminaribiose, chitobiose, mannobiose or sophorose; or maltotriose, isomaltotriose, taltotetraose, maltopentaose, mannotriose or manninotriose.

The polymers or copolymers containing glycoside derivatives disclosed in PCT Application No. 90/04598 can be used for the above method.

There is no limitation in the molecular weight of the polymer or copolymer containing glycoside derivative if said polymer or copolymer is soluble in the reaction medium. A law molecular weight requires much amount of polymers or copolymers, thus taking much time to dissolve them in the reaction medium. Therefore, the molecular weight is preferably more than 3,000.

The concentration of the polymer or copolymer containing glycoside derivatives in the reaction system of the antigen-antibody reaction is suitably determined depending upon the molecular weight of the polymer or copolymer, coexisting additives such as salts, proteins, or saccharides. Generally, the polymer or copolymer is adjusted to be contained in the reaction system in an amount such that the final concentration at the time of reaction is 0.01 to 10.0% (W/V), preferably about 0.1 to 5.0% (W/V), more preferably about 0.5 to 2.0% (w/V). When the concentration of the above polymer or copolymer is less than 0.01% (W/V), the above polymer or copolymer is less effect for accelerating the antigen-antibody reaction. On the other hand, the polymer or copolymer having more than 10.0% (w/v) of the concentration increases in nonspecific reaction with the materials other than the object constituents.

The present invention will be explained in detail hereinbelow with reference to Examples, by which no limitation shall not be given.

EXAMPLE 1

Method for purifying antigen

TP antigens were purified according to a method of the present invention.
1. Reagents and ethers
(1) Buffer solution
(1-1) Phosphate buffered saline (pH:6.5) (hereinafter abbreviated to PBS)

A buffer was prepared from potassium dihydrogen phosphate, sodium dihydrogen phosphate (12 hydrate) and sodium chloride to make phosphate concentration of 0.036M, NaCl concentration of 0.156M and pH 6.5. To this buffer was added $NaN_3$ at a concentration of 0.1% (w/v).

(1-2) 1% BSA/PBS

Bovine serum albumin (hereinafter abbreviated to BSA, manufactured by Miles Laboratories Co.) was dissolved in PBS to make 1% (W/V) BSA solution. (1-3) 10 mM potassium phosphate buffer (pH:6.0 and pH:7.0) (hereinafter abbreviated to KPB)

10 mM potassium dihydrogen phosphate solution was mixed with 10 mM dipotassium hydrogen phosphate to obtain potassium phosphate buffers having pH 6.0 and 7.0.

(1-4) 350 mM KPB (pH:6.0)

350 mM potassium dihydrogen phosphate was mixed with 350 mM dipotassium hydrogen phosphate to obtain mM potassium phosphate buffer having pH 6.0.

(2) Surfactant

Octylglucopyranoside (1-O-n-octyl-β-D-glucopyranoside (hereinafter abbreviated as OG) used for a study of slightly soluble proteins (manufactured by Nacalai Tesque, Inc.) was employed as a surfactant.

(3) Chromatographic gel for purifying protein (3-1) Cation exchanger

Sepharose Fast Flow (Pharmacia LKB Biotechnology), which is cation exchanger wherein a sulfonic acid group was introduced to the surface of agarose gel, was used as cation exchanger.

(3-2) Hydroxyapatite gel

Bio-Gel® HTP (Bio-Rad Laboratories) and HCA-200L (Mitsui Toatsu Chemicals, Inc.) were used as hydroxyapatite gel.

(4) TP

Treponemes were used was cultivated and isolated by the following method.

A suspension of a pathogenic standard Nichols strain of *Treponema pallidum* ($6.0 \times 10^7$/ml) was inoculated in rabbit testes in an amount of 1 ml per testis. After the cultivation for 10 days, testes were taken out from 10 rabbits, sliced and then shaked for 30 minutes at 37° C. in 2.2% sodium citrate solution (500 ml). Thereafter, proliferated treponemes were extracted. The extract was centrifuged for 5 minutes at 200×g to remove the precipitate of rabbit tissue. The supernatant was centrifuged for 30 minutes at 3000×g to precipitate treponemes. Thus obtained treponemes were well washed with PBS and suspended in PBS to adjust the number of the treponemes to $1 \times 10^9$ after the counting with a dark-field microscope. Thus, a suspension of TP mycelia was obtained. This suspension was confirmed with a dark-field microscope that no sperms and tissues of rabbit were included.

(5) Reagent for measuring concentration of protein

BCA® Protein Assay Reagent (Pierce Co.) was used as a reagent for measuring concentration of protein.

(6) Microtiter plate

A microplate having 96 wells (Nunc Co., U-bottom) was used.

(7) TP antigen sensitized erythrocyte

Used sensitized erythrocyte was the one used for Seroclit TP (The Chemo- Sero-Therapeutic Research Institute), which is a TPHA kit on market.

(8) Syphilis-positive serum of rabbit

Used serum was the one taken out from the rabbit which was subjected to the cultivation of TP in its testes for 45 days. Antibody titer was measured by the commercially available TPHA kit, obtaining a value of 102,400. This serum was diluted with 1% BSA/PBS for use.

2. Experimental Method (2-1) Solubilization and extraction of antigen from TP

The suspension of treponemes (10 ml) was washed three times with PBS (50 ml), followed by suspending in PBS (20 ml). The resultant suspension was sonicated for disruption. The suspension was subjected to centrifugation for 30 minutes at 12,600×g to take out the precipitate.

Thus obtained precipitate was washed twice with KPB (10 mM, pH 7.0) using centrifugation for 30 minutes at 12,600×g. Thereafter, KPB (10 mM, pH 7.0) containing OG in 1% (W/V) was added in an amount of 25 ml to the precipitate. The suspension was then slightly sonicated to be solubilized. After being left at 4° C. for 16 hours or more, the mixture was centrifuged for 1 hour at 50,000×g. The resulting supernatant was filtered through a filter of 0.22 μm (Millex-GS produced by Millipore Corporation). The extract obtained from the treponemes in this way was referred to as the extracted antigen hereinbelow.

(2-2) Pretreatment (1) Dialysis of antigen solution

The extracted antigen which was dissolved in a buffer having pH 7.0 was dialyzed against a buffer having pH 6.0 and containing 1% OG. The dialysis was carried out with the volume ratio of the dialyzing solution to the extracted antigen solution being 4 to 1. The dialyzing solution was exchanged three times. After the final dialysis, the pH value of the dialyzing solution (external solution for dialysis) was confirmed to be in the range of from 6.0±0.1.

(2) The antigen obtained in (1) was passed through a column (Pharmacia LKB Biotechnology, SR 25/45) of S Sepharose Gel (30 ml) to collect 50 ml of the passed-through fraction as the antigen fraction (hereinbelow referred to as the partially purified antigen).

(2-3) Purification of antigen by hydroxyapatite gel (1) Washing of hydroxyapatite gel A column (Pharmacia LKB Biotechnology, HR 10/10) was filled with the hydroxyapatite gel (8 ml), followed by equilibrated with 10 mM KPB containing 1% OG (pH 6.0). The optical density (hereinafter abbreviated to O.D.) of the washing solution at 280 nm was measured. Washing was continued until the absorbance of the eluate decreases to 0.010.

(2) Addition of the partially purified antigen

The partially purified antigen was added to a hydroxyapatite column. Thereafter, 10 mM KPB containing 1% OG (pH 6.0) was passed through the column. The column was washed until the absorbance of the eluate solution becomes 0.010 or less at 280 nm. The fraction thus obtained was defined as the passed-through fraction.

(3) Elution of antigen

A linear gradient elution was conducted by gradually increasing the ratio of 350 mM KPB containing 1% OG to 10 mM KPB containing 1% OG (pH 6.0) from 0 to 40%, and finally increasing it to 100% The fractions of the ratios of 0–8%, 8–16%, 16–24% 24–32% and 32–40% were collected. The fraction at the ratio of 100% is defined as the 40% or more fraction.

(4) Assay of each fraction

The antigen activity and protein concentration of each of the extracted antigen, the passed-through fraction, 0–8% fraction, 8–16% fraction, 16–24% fraction, 24–32% fraction, 32–40% fraction and 40% or more fraction were measured by the following methods. Specific activitiy was calculated from the antigen activity and protein concentration.

(2-4) Antigen assay method (1) Protein concentration

The protein concentration was measured by BCA® protein Assay Reagent (Pierce Co.) in which a measuring method [Smith, P. K., Krohn, R. I. etc., (1985) Anal. Biochme. 150, 76–85] was used as its principle. Said measuring method uses bicinchoninic acid and is one of the modified Lawry method. The used standard was a solution of BSA in 10 mM KPB containing 1% OG. The unit was expressed by μg/ml.

(2) Antigen activity (a) 25 μl of 1% BSA/PBS was dispersed in each well of the microtiter plate.

(b) 25 μl of each antigen fraction was dispersed in the well of the plate and 25 μl of it was transferred in the above next well repeatedly to be diluted serially $2^1$ to $2^n$ fold with 1% BSA/PBS on the plate.

(c) Syphilis-positive rabbit serum, in which the antibody titer was diluted to 50 fold, was added to and mixed with the antigen fractions diluted $2^1$ to $2^n$ fold in (b).

(d) The mixture was incubated for 30 minutes or more at room temperature. The antibody in the well having a high concentration of antigen was consumed by antigen-antibody reaction, while the antibody on the well having a low concentration of antigen remained thereon.

(e) Subsequently, TP antigen sensitized erythrocyte in the commercially available TPHA kit (Serodia-TP) was added to each well. A final dilution ratio of the rabbit serum which caused the hemagglutination was defined as the antigen activity. This antigen activity was represented by titer (titer/ml).

(g) Among the fractions exhibiting the antigen activity, those exhibiting a specified activity of 12 titer/μg or more were collected. Thus collected fractions were concentrated under reduced pressure by using cellophane tube (Wako Pure Chemical Industries, Ltd.) until the protein concentration became to 50 μg/ml or more. The obtained fractions were defined as the HAp purified antigen.

3. Other experiments

Antigens were purified with Bio-Gel® HTP and HCA-200 L by the same manner as described above. Besides the antigen activity and protein concentration of each of the fractions, those of extracted antigen and partially purified antigen were measured, whereby total antigen activity, total amount of protein and total specific activity of antigen were calculated. Table 1 shows the results.

4. Conclusion

As is apparent from Table 1, when the TP extract was eluted after adsorbing on the hydroxyapatite gel, the antigens were eluted from Bio-Gel® HTP at a salt concentration of 8% (37.2 mM) to 40% (146.0 mM) and from HCA-200 L at a salt concentration of 8% (37.2 mM) to 32% (118.8 mM). Thus obtained fractions were combined, thereby obtaining the TP antigen of high purity having specific activities of 26.6 and 36.7 (titer/pg) respectively.

TABLE 1-(1)

Purification from Bio-Gel® HTP

| Fractions | Total Antigen Activity (titer) | Total amount of Protein (μg) | Specified Activity of Antigen (titer/μg) |
|---|---|---|---|
| passed-through | 0 | 850 | — |
| 0–8% | 0 | 90 | — |
| 8–16% | 4610 | 170 | 27.1 |
| 16–24% | 9220 | 240 | 38.4 |
| 24–32% | 4610 | 180 | 25.6 |
| 32–40% | 2300 | 190 | 12.1 |
| 40% or more | 0 | 430 | — |
| Total of 8–40% | 20740 | 780 | 26.6 |
| Extracted antigen | 24000 | 4250 | 5.6 |
| Partially purified antigen | 24000 | 2370 | 10.1 |

TABLE 1-(2)

Purification from HCA-200L

| Fractions | Total Antigen Activity (titer) | Total amount of Protein (μg) | Specified Activity of Antigen (titer/μg) |
|---|---|---|---|
| passed-through | 0 | 760 | — |
| 0–8% | 0 | 110 | — |
| 8–16% | 2300 | 120 | 12.1 |
| 16–24% | 9220 | 140 | 65.0 |
| 24–32% | 4610 | 180 | 25.0 |
| 32–40% | 580 | 360 | 1.6 |
| 40% or more | 0 | 700 | — |
| Total of 8–40% | 16130 | 440 | 36.7 |
| Extracted antigen | 24000 | 4250 | 5.6 |
| Partially purified antigen | 24000 | 2370 | 10.1 |

Reference Example 1

Confirmation of protein purity by SDS-PAGE

1. Materials (1) Electrophoretic apparatus

Phastsystem (Pharmacia) was used in accordance with its instruction.

(2) Molecular weight marker

Used molecular weight marker was the LMW kit E manufactured by Pharmacia LKB Biotechnology.

(3) Buffer for treating sample

The buffer was prepared by adding sodium dodecyl sulfate (5%) and mercaptoethanol (10%) to a solution of 10 mM Tris-HCl and 2 mM EDTA (pH 8.0).

(4) Polyacrylamide gel

PhastGel Gradient 10–15 (Phast System) was used.

(5) Staining solution

A high-sensitive argentation solution for electrophoresis "Sil-Best Stain for Protein/PAGE" (Nacalai Tesque, Inc.) was used in accordance with the instruction.

2. Operation Method (1) Preparation of samples

The extracted antigen, partially purified antigen or HAp purified antigen as obtained in Example 1 were mixed with the sample buffer in an equal amount and incubated for 5 minutes at 100° C.

(2) Preparation o#the molecular weight marker

The molecular weight marker was dissolved in the sample buffer which was diluted in two fold with purified water, and then the solution was incubated for 5 minutes at 100° C.

(3) The above-mentioned samples were loaded on the polyacrylamide gel in an amount of 1 μl for electrophoresis.

(4) After electrophoresis, the polyacrylamide gel was stained and the molecular weight of protein was calculated from its position in the gel.

3. Result

About 20 bands were observed in the extracted antigen, while about 10 and 3 bands (at molecular weights of about 31,000, 41,000 and 47,000) were observed in the partially purified antigen and HAp purified antigen respectively.

4. Conclusion

As is apparent from the result, an extremely high-purified TP antigen fraction was obtained by using the hydroxyapatite gel.

Example 2

TPHA

The purified antigen obtained in accordance with the present invention was carried on sheep erythrocyte for confirming the effect of the invention by TPHA.

1. Materials

The same materials as used in Example 1 were used if unspecified. The buffer was prepared by the same manner as in Example 1.

(1) Buffer (a) 0.15M sodium phosphate buffer (pH:7.4):

The buffer was prepared by mixing 0.15M sodium dihydrogen phosphate (2 hydrate) with 0.15M disodium hydrogen phosphate (12 hydrate) so as to show pH 7.4.

(b) Physiological saline solution

The saline solution was prepared by dissolving sodium chloride (9.0 g) in purified water (1000 g).

(c) McIlvaine buffer (hereinafter abbreviated to McI)

McI was prepared by mixing 0.10M citric acid with 0.20M disodium hydrogen phosphate (12 hydrate) so as to show pH 6.5.

(d) 1% OG/McI

The above-identified solution was obtained by dissolving OG (1% W/V) in McI.

(e) PHA buffer

The above-identified buffer was prepared by mixing the solutions and reagents described as follows (The amount is expressed per 1000 ml of buffer.)

| Rabbit normal serum | 30 ml |
|---|---|
| Sheep erythrocyte stroma | 10 ml |
| Sodium azide | 1 g |
| 0.15M sodium phophate buffer (pH 7.4) | 100 ml |
| Physiological saline | 860 ml |

(2) Reagents (a) Tannic acid was bought from Nacalai Tesque, Inc.

(b) Fixed sheep erythrocyte was the one immobilized with glutaraldehyde.

(c) TPHA kits commercially available

Serodia TP (Fuji Rebio Inc.) and Seroclit TP (The Chemo-Sero-Therapeutic Research Institute) were used.

(3) Serum Samples (a) Syphilis-positive control

Three control sera ($G_1$, $G_2$ and $G_3$) were used, those of which were collected from fully cured advanced syphilitic patients. These control sera were supposed to contain a lot of IgG antibodies. Further, three control sera ($M_1$, $M_2$ and $M_3$) were used, those of which were collected from primary syphilitic patients, i.e., three to five weeks after the infection. The latter controls were supposed to contain few Ig-G antibodies, but Ig-M antibodies.

(b) Normal control (Syphilis-negative control)

Three control sera ($N_1$, $N_2$ and $N_3$) were used, those of which were observed to show nonspecific reaction with the TPHA kit commercially available and further found not to be syphilic by FTA-ABS.

(c) Anti-rabbit tissue antiserum

A normal rabbit testis sliced and solubilized with 1% OG was immunized to a goat for obtaining the above-identified serum.

(d) Anti-Reiter strain antiserum

Nonphthogenic treponemes, *Treponema phagedenis* (biotype Reiter), were solubilized with 1% OG. This solution was immunized to a goat for obtaining the above-identified serum.

(4) TP antigen

The extracted antigen, partially purified antigen and HAp purified antigen as obtained in Example 1 were used. Table 2 shows the antigen activity and protein concentration of each antigen solution.

TABLE 2

| Antigen | Antigen Activity (titer/ml) | Protein cocn. (µg/ml) | Specified Activity (titer/µg) |
|---|---|---|---|
| Extracted Antigen | 2048 | 365 | 5.6 |
| Partially purified antigen (HAp Purification) | 1024 | 101 | 10.1 |
| Bio-Gel ® HTP | 2048 | 77.0 | 26.6 |
| HCA-200L | 1536 | 41.9 | 36.7 |

2. Method (1) Blood cell processing method (a) The fixed sheep blood cells were washed four times with a physiological saline by using centrifugation for 5 minutes at 700×g, which was suspended in a physiological saline to have solid content of 6%. A solution (tannic acid in physiological saline, 120 µg/ml) was added to the blood cell suspension, followed by stirring.

(b) After stirring, the resultant solution was washed twice with a physiological saline and once with McI, and then suspended in McI to have solid content of 6%. Immediately, the resultant solution was used for antigen sensitization.

(c) TP antigen solution (the extracted antigen solution, partially purified antigen solution or HAp purified solution) was in advance dialyzed against 1% OG/McI. The obtained solution was adjusted as described in Table 3 to serve as the sensitizing solution. The sensitizing solution A was adjusted to have antigen activity of 100 (titer/ml). The sensitizing solution B was adjusted to have protein concentration of 10 µg/ml. One volume of the sensitizing solution was added to one volume of the blood cell suspension as described at (b) and the mixture was stirred for 1 hour at 25° C.

TABLE 3

| Antigen | Sensitizing Solution A (Sensitization with a predetermined antigen amount) | | Sensitizing Solution B (Sensitization with a predetermined protein amount) | |
|---|---|---|---|---|
| | Antigen Solution (ml) | 1% OG/ McI (ml) | Antigen Solution (ml) | 1% OG/ McI (ml) |
| Extracted | 0.049 | 0.951 | 0.027 | 0.973 |
| Partially purified (HAp purification) | 0.098 | 0.902 | 0.099 | 0.901 |
| Bio-Gel ® HTP | 0.049 | 0.951 | 0.130 | 0.870 |
| HCA-200L | 0.065 | 0.935 | 0.239 | 0.761 |

(d) The sensitized blood cells were washed twice with a physiological saline and suspended in PHA buffer to have blood cell solid content of 0.2%. After standing for 3 hours at room temperature, the resultant suspension was used for assay.

(2) TPHA assay method (a) 100 µl of PHA buffer was dispensed in each well of the microtiter plate, and 25 µl in other wells.

(b) 25 µl of each control was dispensed in each well of the microtiter plate, which was serially diluted $2^1$ to $2^n$ on the plate.

(c) The blood cell suspension prepared in (1) was shaken to obtain a homogeneous suspension. 75 µl of the suspension was dispensed in each well.

(4) The plate was vibrated to mix sufficiently. Thereafter, the plate was covered with an empty plate in order to prevent evaporation and then incubated at room temperature. The determination was conducted after 2 hours.

(5) The plate was placed on white paper, observing hemagglutination by visual observation. The maximum dilution (20, 40, 80, . . . ) exhibiting agglutination was defined as the antibody titer.

3. Result

Table 4 shows the results of determination of hemagglutination on each control and of measurement of antibody titer by using the sensitized blood cell obtained by the above method.

As shown in Table 4, three primary syphilitic sera which were all negative with the sensitized blood cell using the extracted antigen were positive with the sensitized blood cell using the HAp purified antigen of the present invention.. Normal control sera exhibiting nonspecific reaction by the TPHA kit showed no agglutination. Further, the sensitized blood cell using the present invention exhibited no agglutination with the anti-rabbit tissue antiserum and anti-Reiter strain-antiserum.

4. Conclusion

As is apparent from the result, even a primary syphilis is detectable by using the antigen purified according to the present invention, without giving a false positive result due to the nonspecific reaction.

TABLE 4

Result of TPHA

| Antigen Control | | HAp purified antigen Bio-Gel ® HTP | HCA-200L | Partially purified antigen | Extracted antigen | Commercial TPHA |
|---|---|---|---|---|---|---|
| (1) Sensitizing Solution (A) Sensitization with a predetermined antigen amount | | | | | | |
| Primary syphilis | M1 | +<br>×160 | +<br>×160 | ±<br>×80 | −<br>×40 | −<br>×40 |
| | M2 | +<br>×320 | +<br>×320 | +<br>×160 | ±<br>×80 | ±<br>×80 |
| | M3 | +<br>×160 | +<br>×160 | ±<br>×80 | −<br>×40 | −<br>×40 |
| Advanced syphilis | G1 | +<br>×1280 | +<br>×1280 | +<br>×1280 | +<br>×320 | +<br>×320 |
| | G2 | +<br>×640 | +<br>×640 | +<br>×640 | +<br>×320 | +<br>×320 |
| | G3 | +<br>×320 | +<br>×320 | +<br>×160 | ±<br>×80 | ±<br>×80 |
| Normal | N1 | −<br><20 | −<br><20 | −<br><20 | −<br><40 | −<br><40 |
| | N2 | −<br><20 | −<br><20 | −<br>×40 | +<br>×160 | +<br>×160 |
| | N3 | −<br><20 | −<br><20 | −<br>×20 | ±<br>×80 | ±<br>×80 |
| Anti-rabbit tissue antiserum | | −<br><20 | −<br><20 | −<br>×40 | +<br>×160 | −<br>×20 |
| Anti-Reiter strain antiserum | | −<br><20 | −<br><20 | −<br>×40 | +<br>×160 | −<br><20 |
| (2) Sensitizing solution (B) Sensitization with a predetermined protein amount | | | | | | |
| Primary syphilis | M1 | +<br>×160 | +<br>×160 | ±<br>×80 | −<br><20 | −<br>×40 |
| | M2 | +<br>×320 | +<br>×320 | +<br>×160 | −<br>×40 | ±<br>×80 |
| | M3 | +<br>×160 | +<br>×160 | ±<br>×80 | −<br>×40 | −<br>×40 |
| Advanced syphilis | G1 | +<br>×1280 | +<br>×1280 | +<br>×1280 | +<br>×320 | +<br>×320 |
| | G2 | +<br>×640 | +<br>×640 | +<br>×640 | +<br>×160 | +<br>×320 |
| | G3 | +<br>×320 | +<br>×320 | +<br>×160 | ±<br>×40 | ±<br>×80 |
| Normal | N1 | −<br><20 | −<br><20 | −<br><20 | −<br>×40 | −<br>×40 |
| | N2 | −<br><20 | −<br><20 | −<br>×40 | ±<br>×80 | +<br>×160 |
| | N3 | −<br><20 | −<br><20 | −<br>×20 | ±<br>×80 | ±<br>×80 |
| Anti-rabbit tissue antiserum | | −<br><20 | −<br><20 | −<br>×40 | ±<br>×80 | −<br>×20 |
| Anti-Reiter strain antiserum | | −<br><20 | −<br><20 | −<br>×40 | ±<br>×80 | −<br><20 |

+: positive (antibody titer more than 80)
±: false positive (antibody titer of 80)
−: negative (antibody titer less than 80)
The value shown below each result represents an antibody titer.

EXAMPLE 3

Latex reagent (for measuring method using fully-automatic analyzer)

In the case of detecting anti-treponemal antibodies, the effect of the diagnostic latex reagent as prepared by the present invention was confirmed by measuring the agglutination with the use of a fully-automatic analyzer. Controls as those used in Example 1 and Example 2 were prepared by the same manner as in Example 1 and Example 2 if unspecified.

1. Preparation of reagent and control
   (1) Latex
   Polystyrene latex (solid:10%) of 0.400 μm (Sekisui Chemical Co., Ltd.) was used.
   (2) PBS (pH:7.4)
   A solution of 0.02M phosphate and 0.15M sodium phosphate,(2 hydrate), disodium phosphate (2 hydrate) and sodium chloride, to which NaN$_3$ (as preservative) was added at 0.1%.
   (3) NaCl—PBS (pH: 6.5)

A buffer was prepared from sodium phosphate (2 hydrates), disodium phosphate (2 hydrates) and sodium chloride to make phosphate concentration of 0.02M, NaCl concentration of 1.00M and pH 6.5.

(4) 100 mM NaPB

A solution of 100 mM NaPB (pH:7.5) were prepared from disodium hydrogen phosphate (anhydrous) and sodium dihydrogen phosphate (12 hydrate), to which $NaN_3$ was added at 0.1%.

(5) 1% BSA—NaPB

The above-identified solution was prepared to have BSA in 100 mM NaPB. (6) 5% BSA—NaPB The above-identified solution was prepared to have 5% BSA in 100 mM NaPB.

(7) Diluent

The diluent was prepared by dissolving polyethylene glycol (average molecular weight:500,000, Wako Pure Chemical Industries, Ltd.) in 0.25% (W/V) in BSA—NaPB.

(8) Instrument

Measurement was performed on Hitachi 7050 Type, a fully-automatic analyzer.

2. Method (1) Preparation of antigen sensitizing solution

To each antigen solution having antigen titer and protein concentration shown in Table 2 was added a mixture of 10 mM KPB, of NaCl—PBS and 1% OG in the amount shown in Table 5. The obtained solution was defined as the sensitizing solution (the antigen solution for immobilization) having pH 5.4 to 6.5. The sensitizing solution A was prepared to have antigen activity of 250 (titer/ml), while the sensitizing solution B was prepared to have protein concentration of about 25 μg/ml.

TABLE 5

Sensitizing solution A
(Sensitization with a predetermined antigen amount)

| Antigen | Antigen Solution (ml) | 1% OG/KPB pH 6.0 (ml) | NaCl/PB (ml) |
|---|---|---|---|
| Extracted antigen | 0.049 | 0.251 | 0.100 |
| Partially purified antigen (HAp purification) | 0.098 | 0.202 | 0.100 |
| HCA-200L | 0.049 | 0.251 | 0.100 |
| Bio-Gel ® HTP | 0.065 | 0.235 | 0.100 |

Sensitizing solution B
(Sensitization with a predetermined protein amount)

| Antigen | Antigen Solution (ml) | 1% OG/KPB pH 6.0 (ml) | NaCl/PB (ml) |
|---|---|---|---|
| Extracted antigen | 0.027 | 0.273 | 0.100 |
| Partially purified antigen (HAp purification) | 0.099 | 0.201 | 0.100 |
| HCA-200L | 0.130 | 0.170 | 0.100 |
| Bio-Gel ® HTP | 0.239 | 0.061 | 0.100 |

(2) Immobilization of treponemal antigen

Polystyrene Latex (100 μl) (solid content of 10% by weight) was stirred by a magnetic stirrer in an incubator at 4° C., with which the treponemal antigen solution (400 μl) prepared in (1) was quickly mixed and stirred for 1 hour at 4° C. After the addition of 1% BSA (5 ml), the resultant mixture was stirred for 1.5 hours at 4° C. and then centrifuged for 1 hour at 15,000 rpm. To the obtained pellets was added again 1% BSA—NaPB (5 ml). The resultant mixture was centrifuged by the same manner as described above and washed. 1% BSA—NaPB (5 ml) was added to the final pellets and sufficiently dispersed, thereby affording latex reagent having solid content of 0.2%. Thus obtained Latex reagent was kept at 4° C.

(3) Parameters of Hitachi 7050 Type, a fully-automatic analyzer

| | |
|---|---|
| Sample content | 20 μl (serum) |
| R1 content | 50 μl (Latex reagent) |
| R2 content | 350 μl (diluent) |
| Wavelength | 570 nm |

(4) Measuring method

The difference of the absorbance between 80 seconds after the beginning of the measurement and 320 seconds after the beginning of the measurement was taken. $10^4$ of this difference was defined as the variation at O.D. 570.

3. Result

The reaction of each control with the Latex reagent prepared from the TP antigen solution by the manner described above was measured as the variation of turbidity at O.D. 570. Table 6 shows the results.

As shown in Table 6, three primary syphilitic sera which were all negative with the latex reagents using the extracted antigen and partially purified antigen exhibited sensitivity sufficient for determining to be positive with the latex reagent using the purified TP antigen of the present invention. Three advanced syphilitic sera exhibiting nonspecific reaction with the TPHA kit showed no agglutination with the latex reagent using the purified TP antigen of the present invention. Further, the latex reagent using the present invention did not exhibit a turbidity for determining to be positive with the anti-rabbit tissue antiserum and anti-Reiter strain antiserum.

4. Conclusion

As is apparent from the result, the reagent prepared from the purified antigen according to the present invention is more reactive, i.e., high-sensitive compared to there from the conventional extracted antigen. As a result, even primary syphilis, which cannot be detected by the conventional extracted antigen can be detected by using the purified antigen according to the present invention.

Further, the use of the purified antigen can detect primary syphilis, which cannot be detected by the commercially available TPHA kit, and also does not give the false positive result by the nonspecific reaction.

TABLE 6

| | | Result with a latex reagent | | | |
|---|---|---|---|---|---|
| | | HAp purified antigen | | Partially | Ex- |
| Antigen Control | | Bio-Gel ® HTP | HCA-200L | purified antigen | tracted antigen |
| Sensitizing Solution (A) Sensitization with a predetermined antigen amount | | | | | |
| Primary syphilis | M1 | 323 | 639 | 157 | 44 |
| | M2 | 857 | 1433 | 184 | 103 |
| | M3 | 646 | 626 | 108 | 38 |
| Advanced syphilis | G1 | 2101 | 3289 | 1624 | 678 |
| | G2 | 1655 | 2273 | 683 | 275 |
| | G3 | 849 | 1274 | 154 | 110 |
| Normal | N1 | 4 | 2 | 19 | 55 |

TABLE 6-continued

| | | Result with a latex reagent | | | |
|---|---|---|---|---|---|
| | | HAp purified antigen | | Partially | Ex- |
| Antigen | | Bio-Gel ® | | purified | tracted |
| Control | | HTP | HCA-200L | antigen | antigen |
| | N2 | 3 | 5 | 16 | 21 |
| | N3 | 2 | 7 | 19 | 21 |
| Anti-rabbit tissue antiserum | | 3 | 3 | 40 | 105 |
| Anti-Reiter strain antiserum | | 5 | 9 | 32 | 97 |
| Sensitizing Solution (B) Sensitization with a predetermined protein amount | | | | | |
| Primary | M1 | 1231 | 1710 | 161 | 16 |
| syphilis | M2 | 3144 | 3882 | 171 | 41 |
| | M3 | 1231 | 1695 | 122 | 21 |
| Advanced | G1 | 7812 | 7540 | 1585 | 291 |
| syphilis | G2 | 6129 | 6148 | 652 | 100 |
| | G3 | 3102 | 3225 | 171 | 65 |
| Normal | N1 | 5 | 3 | 317 | 5 |
| | N2 | 2 | 2 | 15 | 3 |
| | N3 | 3 | 7 | 19 | 10 |
| Anti-rabbit tissue antiserum | | 9 | 6 | 39 | 66 |
| Anti-Reiter strain antiserum | | 5 | 8 | 41 | 35 |

EXAMPLE 4

Assay for syphilis antibody by ELISA method

The effect of the purified antigen of the present invention was confirmed by ELISA method.

1. Preparation of reagent and control

The following reagents and controls were prepared for use. The same reagents and controls as those used in Examples 1, 2 and 3 were prepared by the same manner as in Examples 1, 2 and 3.

(1) TP antigen solution

Used antigen solution were the extracted antigen, partially purified antigen and HAp purified antigen obtained in Example 1.

(2) Control

The controls used in Example 2 were diluted by a hundred fold with 1% BSA/PBS.

(3) Peroxidase labelled anti-goat Ig-G

Peroxidase labelled anti-goat Ig-G (originated from sheep) (Miles Laboratories Co.) was diluted by a thousand fold with 1% BSA/PBS without NaN$_3$.

(4) Peroxidase labelled anti-human Ig-G and Ig-M

Peroxidase labelled anti-goat Ig-G and Ig-M (originated from sheep) (Miles Laboratories Co.) were diluted by a thousand fold with 1% BSA/PBS without NaN$_3$.

(5) Microtiter plate

A microtiter plate having 96 wells (Nunc Co., flat bottom for ELISA) was used.

(6) Peroxidase substrate o-Phenylenediamine (dihydrochloride) (2 mg/ml) and aqueous hydrogen peroxide (0.03%) were dissolved in a phosphoric acid-citric acid buffer (pH 5.0). The substrate was prepared immediately before being used.

(7) Stop solution 1N sulfuric acid solution was used as the stop solution of enzyme reaction.

2. Method (1) Preparation of antigen solution

By the same manner as in Example 3, to each antigen solution was added a mixture of 10 mM KPB, NaCl—PB and 1% OG in the amount shown in Table 7.

TABLE 7

(Composition of sensitizing solution for ELISA)

| Antigen | Antigen Solution (ml) | 1% OG/KPB (ml) | NaCl/PBS (ml) |
|---|---|---|---|
| Sensitizing solution A (Sensitization with a predetermined antigen amount) | | | |
| Extracted antigen | 0.049 | 0.351 | 0.100 |
| Partially purified antigen (HAp purification) | 0.098 | 0.302 | 0.100 |
| HCA-200L | 0.049 | 0.351 | 0.100 |
| Bio-Gel ® HTP | 0.065 | 0.335 | 0.100 |
| Sensitizing solution B (Sensitization with a predetermined protein amount) | | | |
| Extracted antigen | 0.027 | 0.373 | 0.100 |
| Partially purified antigen (HAp purification) | 0.099 | 0.301 | 0.100 |
| HCA-200L | 0.130 | 0.270 | 0.100 |
| Bio-Gel ® HTP | 0.239 | 0.161 | 0.100 |

(2) Immobilization of the TP antigen

The TP antigen solution prepared in (1) was dispersed into the microtiter plate in an amount of 50 μl and incubated for 1 hour at room temperature.

After the incubation, the excess TP antigen solution was removed and washed three times with 1% BSA/PBS (200 μl) under suction. Thereafter, 1% BSA/PBS (200 μl) was added to the resultant and incubated for 1 hour at room temperature for effecting blocking. The plate to which blocking was completed was used for antigen-antibody reaction.

(3) Antigen-antibody reaction

As a first antibody, the control diluted hundredfold with 1% BSA/PBS was pipetted into each well in an amount of 100 μl. As a control, the control was similarly pipetted into each well to which 1% BSA/PBS was added instead of the antigen. After incubated for 1 hour at room temperature, the solution was removed under suction and washed three times with 1% BSA/PBS (200 μl) under suction.

Then, the peroxidase labelled anti-human Ig-G and anti-human Ig-M were pipetted in an amount of 100 μl into each well into which the primary syphilis sera, advanced syphilis sear and syphilis-negative sear were pipetted. Further, the anti-goat Ig-G was pipetted in an amount of 100 μl into each well into which the anti-Reiter strain antiserum and anti-rabbit tissue antiserum were pipetted. After the incubation for 1 hour at room temperature, each well was sucked and washed three times with 200 μl of 1% BSA/PBS. Immediately after washing, enzyme activity bound to each well was measured.

(4) Enzymatic reaction

100 μl of peroxidase substrate was added to each well and the plate was incubated for 15 minutes at room temperature. As a substrate blank, the substrate was pipetted into each well not containing antigen, first antibody or second antibody. After the incubation, 1N stop solution (100 μl) was added to stop the enzymatic reaction. After stopping the reaction, the absorbance at 492 nm was measured with a microtiter plate reader (MTP-100, Corona Electric Co., Ltd.), in comparison with the substrate blank.

3. Result

Table 8 shows the results of the absorbance at 492 nm.

Three primary syphilitic sear increase in detection sensitivity of IgM by using the purified antigen of the present invention. Three syphilis-negative controls exhibit falsely positive (the value of more than O.D. 0.057 is determined to be positive) by using the extracted antigen, while do not exhibit positive by using the purified antigen of the present invention.

Moreover, the purified antigen of the present invention did not show a value for determining to be positive with the anti-rabbit tissue antiserum and anti-Reiter strain antiserum.

4. Conclusion

As is apparent from the above result, the purified antigen according to the present invention can detect even primary syphilis, which can not be detected by ELISA method using the conventional extracted antigen, and also does not give a false positive result by the nonspecific reaction.

TABLE 8

Result of ELISA

| | | HAp purified antigen | | | | Partially | | | |
| | | Bio-Gel ® HTP | | HCA-200L | | purified antigen | | Extracted antigen | |
| Antigen | | | | | | | | | |
| Control | 1st antibody | anti Ig-G | anti Ig-M | anti Ig-G | anti Ig-M | anti Ig-G | anti Ig-M | anti Ig-G | anti Ig-M |
| (1) Sensitizing Solution (A) Sensitization with a predetermined antigen amount | | | | | | | | | |
| Primary syphilis | M1 | 0.125 | 0.452 | 0.182 | 0.518 | 0.123 | 0.257 | 0.050 | 0.030 |
| | M2 | 0.098 | 0.258 | 0.082 | 0.210 | 0.102 | 0.220 | 0.056 | 0.062 |
| | M3 | 0.058 | 0.142 | 0.064 | 0.264 | 0.045 | 0.084 | 0.057 | 0.042 |
| Advanced syphilis | G1 | 0.984 | 0.245 | 0.845 | 0.214 | 0.789 | 0.145 | 0.874 | 0.168 |
| | G2 | 1.489 | 0.478 | 1.378 | 0.347 | 1.540 | 0.210 | 1.554 | 0.355 |
| | G3 | 0.258 | 0.154 | 0.321 | 0.148 | 0.265 | 0.081 | 0.291 | 0.067 |
| Negative syphilis | N1 | 0.015 | 0.014 | 0.012 | 0.016 | 0.032 | 0.024 | 0.064 | 0.056 |
| | N2 | 0.020 | 0.016 | 0.009 | 0.013 | 0.051 | 0.024 | 0.224 | 0.095 |
| | N3 | 0.021 | 0.012 | 0.013 | 0.016 | 0.042 | 0.032 | 0.102 | 0.081 |
| Anti-rabbit tissue antiserum | | 0.009 | — | 0.015 | — | 0.104 | — | 0.278 | — |
| Anti-Reiter strain antiserum | | 0.015 | — | 0.012 | — | 0.069 | — | 0.225 | — |
| (2) Sensitizing solution (B) Sensitization with a predetermined protein amount | | | | | | | | | |
| Primary syphilis | M1 | 0.138 | 0.513 | 0.173 | 0.476 | 0.138 | 0.289 | 0.042 | 0.046 |
| | M2 | 0.082 | 0.376 | 0.099 | 0.410 | 0.132 | 0.253 | 0.043 | 0.051 |
| | M3 | 0.043 | 0.227 | 0.061 | 0.232 | 0.035 | 0.075 | 0.045 | 0.057 |
| Advanced syphilis | G1 | 0.965 | 0.233 | 0.846 | 0.256 | 0.822 | 0.109 | 0.278 | 0.078 |
| | G2 | 1.625 | 0.489 | 1.478 | 0.512 | 1.579 | 0.224 | 0.456 | 0.125 |
| | G3 | 0.289 | 0.167 | 0.335 | 0.154 | 0.258 | 0.084 | 0.085 | 0.054 |
| Negative syphilis | N1 | 0.013 | 0.012 | 0.009 | 0.006 | 0.045 | 0.030 | 0.102 | 0.048 |
| | N2 | 0.016 | 0.013 | 0.015 | 0.008 | 0.051 | 0.014 | 0.152 | 0.054 |
| | N3 | 0.017 | 0.018 | 0.016 | 0.006 | 0.038 | 0.031 | 0.106 | 0.043 |
| Anti-rabbit tissue anti-serum | 0.014 | — | 0.012 | — | 0.067 | — | 0.156 | — | |
| Anti-Reiter strain antiserum | 0.009 | — | 0.008 | — | 0.078 | — | 0.115 | — | |

Average value at O.D. 492 nm (n = 4)

Reference Example 2

Confirmation of antigen protein by immunoplotting assay

1. Reagent and sample

The same reagents and samples as those used in Example 1, Reference Example 1 and Example 4 were prepared by the same manner as these Examples.

(1) Buffer for blotting

The buffer was prepared by mixing 25 mM Tris buffer, 192 mM glycine and 20% methanol to have pH 8.3.

(2) Nitrocellulose membrane (hereinafter abbreviated to NC)

Used membrane was 9×12 cm sheet having a pore size of 0.45μ (Bio-Rad Laboratories).

(3) Syphilis-positive serum

Pooled primary syphilitic serum and advanced syphilitic serum were used.

(4) Peroxidase substrate

4-Chloro-1-naphtol (Nacalai Tesque Inc.) (10 mg) was dissolved in ice-cooled methanol (3.34 ml) and then mixed with citrate phosphate buffer (pH:6.0, 16.66 ml). To the resultant mixture was added 30% aqueous hydrogen peroxide (10 μl) immediately before being used. The substrate was used immediately after preparation.

2. Operation method (1) Phast System® (Pharmacia LKB Biotechnolgy) was used in accordance with its instruction. Electrophoresis of the extracted antigen, partially purified antigen and HAp purified antigen was conducted by the same manner as in Example 2. The same five gels obtained by the electrophoresis were prepared.

(2) NC were in advance immersed in the buffer for blotting to be equilibrated. The NC were pleased on the gel for transferring protein from the gel to NC by electrophoresis with blotting.

(3) After washing three times with PBS, NC were immersed in PBS buffer containing 3% BSA for blocking.

(4) The primary syphilitic serum, advanced syphilitic serum, normal (syphilis-negative) serum, anti-rabbit tissue antiserum and anti-Reiter strain antiserum were diluted hundred fold with 1% BSA/PBS. Each serum was reacted with each antigen transferred onto the above-mentioned NC.

(5) After washing three times with 1% BSA/PBS, the NC reacted with the primary syphilitic serum, advanced syphilitic serum and normal serum were immersed in 1% BSA/PBS containing the peroxidase labelled anti-human Ig-G and anti-human Ig-M for reaction. Similarly, the NC reacted with the anti-Reiter strain antiserum and anti-rabbit tissue antiserum were immersed in 1% BSA/PBS containing the anti-goat Ig-G conjugated with peroxidese for reaction. After the incubation for 1 hour at room temperature, the NC were washed three times with PBS, and immediately after that, enzyme activity bounded to each NC was observed.

(6) Peroxidase substrate was added to the NC and incubated at room temperature. When a suitable colored image was observed, the membranes were washed with purified water and dried. Thereafter, the position and degree of the color development were observed.

3. Result

It was confirmed that three bands (at the vicinity of the molecular weights 31,000, 41,000 and 47,000) of the HAp purified antigen were proteins specifically reactive with syphilis-positive serum only. The bands reacted with the anti-rabbit tissue-antiserum and anti-Reiter strain antiserum were observed in the extracted antigen and partially purified antigen, while such bands were not found in the HAp purified antigen.

4. Conclusion

As is apparent from the result, the TP purified antigen obtained by using the hydroxyapatite gel is a high-pure antigen solution consisting of the component specifically reactive with the syphilis-positive serum only.

EXAMPLE 5

Conditions for adsorption to and elution by hydroxyapatite gel

The partially purified antigen solution obtained in Example 1 was used. Before adding to a column, the buffer of the partially purified antigen solution was exchanged to the buffer for adsorption by dialysis.

Bio-Gel® HTP (Bio-Rad) was used as hydroxyapatite gel.

Other reagents and conditions and methods for chromatography are the same as those in Example 1.

Antigen purity (specific activity) in the obtained fractions were observed by varying the conditions for adsorption and elution by use of Bio-Gel®HTP. Table 9 shows the result.

TABLE 9

| Buffer | | | | | |
|---|---|---|---|---|---|
| Solution A (Adsorption) | | Solution B (Elution) | | Fraction | Specific |
| pH | phosphate conc. | pH | Phosphate conc. | (ratio of B, %) | Activity (titer/μg) |
| 5.5 | 10 mM | 5.5 | 350 mM | 15–50 | 27.5 |
| 6.0 | 10 mM | 6.0 | 350 mM | 8–40 | 28.4 |
| 6.5 | 5 mm | 6.5 | 350 mM | 2–20 | 20.3 |
| 7.0 | 5 mM | 7.0 | 350 mM | 1–5 | 17.2 |
| 6.0 | 10 mM | 8.0 | 10 mM | 10–40 | 19.7 | note: Solution A and B are potassium phosphate buffer containing 1% OG.

EXAMPLE 6

Latex reagent

The partially purified antigen solution obtained in Example 1 was used which was dissolved in 10 mM potassium phosphate buffer (pH:6.0) containing 1% OG. Sensitizing solution having protein concentration of 30μg/ml, predetermined OG concentration and pre-determined pH was prepared by diluting the antigen solution with buffer or adding OG to the antigen solution.

Latex reagent was prepared by the same manner as in Example 3.

Used control was obtained by diluting rabbit serum with phosphate buffered saline [0.02M phosphate buffer, 0.13M sodium chloride (pH:7.4) and 0.1% sodium azide] containing 1% BSA.

The controls were measured with the obtained latex reagent by the same manner as in Example 3. Table 10 shows the result.

TABLE 10

| Sensitizing solution | | % for | Variation | |
|---|---|---|---|---|
| cocn. of OG (%) | pH | dilution (%) | syphilis-negative | syphilis-positive |
| 0.5 | 5.0 | 400 | 8.0 | 205.2 |
|  |  | 200 | 6.0 | 423.0 |
|  |  | 100 | 7.0 | 1024.0 |
| 0.5 | 6.0 | 400 | 3.0 | 237.0 |
|  |  | 200 | 5.0 | 481.2 |
|  |  | 100 | 13.0 | 1312.0 |
| 0.5 | 7.0 | 400 | 10.0 | 225.0 |
|  |  | 200 | 9.0 | 453.6 |
|  |  | 100 | 7.0 | 1200.0 |
| 0.5 | 7.5 | 400 | 4.0 | 186.6 |
|  |  | 200 | 7.0 | 372.0 |
|  |  | 100 | 12.0 | 960.0 |
| 0.025 | 6.0 | 400 | 6.0 | 198.0 |
|  |  | 200 | 11.0 | 420.0 |
|  |  | 100 | 10.0 | 1200.0 |
| 1.0 | 6.0 | 400 | 7.0 | 177.0 |
|  |  | 200 | 8.0 | 372.0 |
|  |  | 100 | 6.0 | 1088.0 |
| 2.0 | 6.0 | 400 | 3.0 | 192.0 |
|  |  | 200 | 6.0 | 378.0 |
|  |  | 100 | 9.0 | 1016.0 | note:
Controls are syphilis-negative and syphilis-positive (10,000 titer) rabbit serum.

TABLE 10-continued

| Sensitizing solution | | % for | Variation | |
|---|---|---|---|---|
| cocn. of OG (%) | pH | dilution (%) | syphilis-negative | syphilis-positive |

Four hundred fold, two hundred fold and one hundred fold the syphilis-positive serum respectively correspond to 25, 50 and 100 titer.

What is claimed is:

1. A process for preparing a purified syphilis antigen which comprises adsorbing an extract originated from *Treponema pallidum* on a hydroxyapatite gel, eluting with an aqueous medium containing octylglucopyranoside and recovering the purified syphilis antigen.

2. The process of claim 1, in which the adsorption is conducted with an aqueous medium having a pH of 5.0 to 8.0 and an ionic strength of 2 to 30 mM.

3. The process of claim 1, in which the elution is conducted with an aqueous medium having a pH of 5.0 to 11.0 and an ionic strength of 10 to 360 mM.

4. The process of claim 1 or 2, in which the elution is conducted with an aqueous medium having either a pH or an ionic strength which is higher than the pH or the ionic strength of the aqueous medium used for the adsorption.

5. The process of claim 1 in which the aqueous medium is phosphate buffer.

6. The process of claim 1 in which the elution is conducted with a linear gradient.

* * * * *